US010064759B2

(12) United States Patent
Locke et al.

(10) Patent No.: US 10,064,759 B2
(45) Date of Patent: Sep. 4, 2018

(54) REDUCED-PRESSURE WOUND DRESSINGS AND SYSTEMS FOR RE-EPITHELIALIZATION AND GRANULATION

(71) Applicant: KCI Licensing, Inc., San Antonio, TX (US)

(72) Inventors: Christopher Brian Locke, Bournemouth (GB); Timothy Mark Robinson, Basingstoke (GB); Richard Daniel John Coulthard, Verwood (GB)

(73) Assignee: KCI Licensing, Inc., San Antonio, TX (US)

(*) Notice: Subject to any disclaimer, the term of this patent is extended or adjusted under 35 U.S.C. 154(b) by 74 days.

(21) Appl. No.: 14/135,120

(22) Filed: Dec. 19, 2013

(65) Prior Publication Data

US 2014/0107600 A1    Apr. 17, 2014

Related U.S. Application Data

(62) Division of application No. 12/857,179, filed on Aug. 16, 2010.

(Continued)

(51) Int. Cl.
*A61F 13/00* (2006.01)
*A61F 13/02* (2006.01)
(Continued)

(52) U.S. Cl.
CPC .... *A61F 13/00068* (2013.01); *A61F 13/0203* (2013.01); *A61M 1/0088* (2013.01); *A61M 27/00* (2013.01)

(58) Field of Classification Search
USPC .......................................................... 604/319
See application file for complete search history.

(56) References Cited

U.S. PATENT DOCUMENTS

| 1,355,846 A | 10/1920 | Rannells |
|---|---|---|
| 2,547,758 A | 4/1951 | Keeling |

(Continued)

FOREIGN PATENT DOCUMENTS

| AU | 550575 A1 | 3/1986 |
|---|---|---|
| AU | 745271 | 4/1999 |

(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).

(Continued)

*Primary Examiner* — Todd J Scherbel
*Assistant Examiner* — Guy K Townsend (57) ABSTRACT

Methods for promoting re-epithelialization and granulation as an aspect of wound healing are presented. A method for promoting granulation and re-epithelialization of a wound at the same time involves using a reduced-pressure treatment dressing and applying a moist, water-sensitive barrier to promote re-epithelialization and to inhibit granulation. Other methods are also presented.

16 Claims, 3 Drawing Sheets

Related U.S. Application Data (60) Provisional application No. 61/237,504, filed on Aug. 27, 2009.

(51) Int. Cl.
  *A61M 1/00* (2006.01)
  *A61M 27/00* (2006.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielson | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,018,515 A * | 5/1991 | Gilman | A61F 13/0276 602/45 |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,106,629 A * | 4/1992 | Cartmell | A61F 13/0203 424/443 |
| 5,134,994 A | 8/1992 | Say | |
| 5,149,331 A | 9/1992 | Ferdman et al. | |
| 5,160,315 A * | 11/1992 | Heinecke | A61F 13/023 206/441 |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,356,372 A * | 10/1994 | Donovan | A61F 13/023 602/41 |
| 5,358,494 A | 10/1994 | Svedman | |
| 5,423,737 A * | 6/1995 | Cartmell | A61F 13/023 206/440 |
| 5,437,622 A | 8/1995 | Carion | |
| 5,437,651 A * | 8/1995 | Todd | A61M 1/0088 15/420 |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 5,844,013 A * | 12/1998 | Kenndoff | A61F 13/0273 521/137 |
| 6,071,267 A | 6/2000 | Zamierowski | |
| 6,135,116 A | 10/2000 | Vogel et al. | |
| 6,201,164 B1 * | 3/2001 | Wulff | A61K 9/0014 602/41 |
| 6,241,747 B1 | 6/2001 | Ruff | |
| 6,287,316 B1 | 9/2001 | Agarwal et al. | |
| 6,345,623 B1 * | 2/2002 | Heaton | A61F 13/023 128/897 |
| 6,420,622 B1 * | 7/2002 | Johnston | A47L 9/02 428/167 |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,566,575 B1 * | 5/2003 | Stickels | A61F 13/023 602/41 |
| 6,685,681 B2 * | 2/2004 | Lockwood | A61M 1/0058 502/43 |
| 6,814,079 B2 | 11/2004 | Heaton et al. | |
| 7,004,915 B2 * | 2/2006 | Boynton | A61M 1/0031 601/6 |
| 7,070,584 B2 * | 7/2006 | Johnson | A61M 1/0088 424/444 |
| 7,651,484 B2 * | 1/2010 | Heaton | A61M 1/0088 604/304 |
| 8,172,816 B2 * | 5/2012 | Kazala, Jr. | A61L 15/60 602/41 |
| 2001/0043943 A1 * | 11/2001 | Coffey | A61F 13/02 424/447 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0132540 A1 * | 9/2002 | Soerens | A61L 15/60 442/59 |
| 2002/0143286 A1 | 10/2002 | Tumey | |
| 2002/0161346 A1 * | 10/2002 | Lockwood | A61M 1/0058 604/315 |
| 2003/0203011 A1 * | 10/2003 | Abuelyaman | A61K 6/10 424/445 |
| 2003/0232905 A1 * | 12/2003 | Ives | C08K 5/0008 524/35 |

(56) References Cited

U.S. PATENT DOCUMENTS

| | | | | |
|---|---|---|---|---|
| 2004/0030304 | A1* | 2/2004 | Hunt | A61M 1/0088 604/317 |
| 2004/0162512 | A1* | 8/2004 | Liedtke | A61F 13/0203 602/59 |
| 2004/0243073 | A1* | 12/2004 | Lockwood | A61M 1/0084 604/313 |
| 2005/0037194 | A1* | 2/2005 | Greene | A61L 15/26 428/364 |
| 2005/0064021 | A1* | 3/2005 | Rippon | A61L 15/26 424/445 |
| 2005/0085795 | A1* | 4/2005 | Lockwood | A61M 1/0084 604/543 |
| 2005/0137539 | A1* | 6/2005 | Biggie | A61M 1/0088 604/313 |
| 2005/0228329 | A1* | 10/2005 | Boehringer | A61F 13/00021 602/52 |
| 2006/0041247 | A1* | 2/2006 | Petrosenko | A61F 13/00 604/543 |
| 2006/0079852 | A1 | 4/2006 | Bubb et al. | |
| 2006/0155260 | A1* | 7/2006 | Blott | A61M 1/0058 604/543 |
| 2006/0173253 | A1* | 8/2006 | Ganapathy | A61B 5/0059 600/310 |
| 2006/0189910 | A1* | 8/2006 | Johnson | A61F 13/0203 602/42 |
| 2006/0264796 | A1* | 11/2006 | Flick | A61F 13/00063 602/48 |
| 2007/0055209 | A1* | 3/2007 | Patel | A61F 13/00063 604/315 |
| 2007/0185426 | A1* | 8/2007 | Ambrosio | A61L 27/52 602/43 |
| 2007/0219532 | A1* | 9/2007 | Karpowicz | A61M 1/0031 604/540 |
| 2008/0011368 | A1* | 1/2008 | Singh | A61M 1/0088 137/565.01 |
| 2008/0039763 | A1* | 2/2008 | Sigurjonsson | A61F 13/0203 602/56 |
| 2008/0076844 | A1* | 3/2008 | Van Sumeren | A61L 15/24 521/137 |
| 2008/0215020 | A1* | 9/2008 | Reeves | A61F 13/00068 604/305 |
| 2008/0300555 | A1* | 12/2008 | Olson | A61F 13/0203 604/313 |
| 2009/0043268 | A1* | 2/2009 | Eddy | A61M 1/0037 604/290 |
| 2009/0254066 | A1* | 10/2009 | Heaton | A61M 1/0011 604/543 |
| 2009/0275922 | A1* | 11/2009 | Coulthard | A61M 1/0088 604/543 |
| 2009/0306630 | A1* | 12/2009 | Locke | A61M 1/0001 604/543 |
| 2010/0069885 | A1* | 3/2010 | Stevenson | A61M 1/008 604/540 |
| 2010/0125258 | A1* | 5/2010 | Coulthard | A61F 13/0203 604/319 |
| 2011/0230848 | A1* | 9/2011 | Manwaring | A61M 1/0088 604/290 |
| 2011/0288512 | A1* | 11/2011 | Locke | A61M 1/0066 604/319 |
| 2012/0016323 | A1* | 1/2012 | Robinson | A61M 1/0031 604/319 |
| 2012/0046624 | A1* | 2/2012 | Locke | A61M 1/0001 604/319 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/010424 | 9/1990 |
| WO | 93/09727 | 5/1993 |
| WO | 94/020041 | 9/1994 |
| WO | 96/05873 | 2/1996 |
| WO | 97/18007 | 5/1997 |
| WO | 99/13793 | 3/1999 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), vol. 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

(56) References Cited

OTHER PUBLICATIONS

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, p. 1.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., vol. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovic, V. Ðukić, Ž. Maksimović, Ð. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, "An Improved Sump Drain-Irrigation Device of Simple Construction," Archives of Surgery 105 (1972) pp. 511-513.

C.E. Tennant, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians (Jul. 2007).

* cited by examiner

REDUCED-PRESSURE WOUND DRESSINGS AND SYSTEMS FOR RE-EPITHELIALIZATION AND GRANULATION

RELATED APPLICATION

This application is a divisional of U.S. patent application Ser. No. 12/857,179, filed Aug. 16, 2010, which claims the benefit, under 35 USC § 119(e), of the filing of U.S. Provisional Patent Application Ser. No. 61/237,504 entitled "Reduced-Pressure Wound Dressings and Systems For Re-Epithelialization and Granulation," filed Aug. 27, 2009, which is incorporated herein by reference for all purposes.

BACKGROUND

The present disclosure relates generally to medical treatment systems and, in particular but not by way of limitation, to reduced-pressure wound dressings, systems, and methods for re-epithelialization and granulation of a wound.

The physiological process of wound healing involves different phases that may occur simultaneously or sequentially. As used herein, "or" does not require mutual exclusivity. Two phases of the wound healing process involve granulation (proliferation) and re-epthiliazation.

SUMMARY

Improvements to certain aspects of wound care dressings, methods, and systems are addressed by the present invention as shown and described in a variety of illustrative, non-limiting embodiments herein. According to an illustrative, non-limiting embodiment, a method for promoting granulation and re-epithelialization of a wound includes the steps of providing a reduced-pressure treatment dressing having a first side and a second, tissue-facing side. The second, tissue-facing side of the reduced-pressure treatment dressing has a micro-strain inducing surface. The method further includes the steps of creating a moist, water-sensitive barrier on portions of the wound to promote re-epithelialization and to inhibit granulation; placing the reduced-pressure treatment dressing adjacent to the wound; and causing a fluid seal over the reduced-pressure treatment dressing. The method also includes applying reduced pressure to the reduced-pressure treatment dressing.

According to an illustrative, non-limiting embodiment, a system for promoting granulation and re-epithelialization of a wound of a patient includes a reduced-pressure treatment dressing and a moist, water-sensitive barrier disposed adjacent the reduced-pressure treatment dressing at portions of the wound to promote re-epithelialization and to inhibit granulation. The system further includes a sealing member for placing over the reduced-pressure treatment dressing and a portion of epidermis of the patient and a reduced-pressure source for providing reduced pressure to the reduced-pressure treatment dressing.

According to an illustrative, non-limiting embodiment, a kit for deploying a dressing for promoting granulation and re-epithelialization of a wound of a patient includes a reduced-pressure treatment dressing and a water-sensitive, flowable material for disposing adjacent to the reduced-pressure treatment dressing at portions of the wound to promote re-epithelialization and to inhibit granulation. The kit also includes a sealing member for placing over the reduced-pressure treatment dressing and a portion of epidermis of the patient. The kit may also include a reduced-pressure delivery conduit for providing reduced pressure to the reduced-pressure treatment dressing. Finally, the kit includes a delivery device for applying the water-sensitive, flowable material.

Other features and advantages of the illustrative, non-limiting embodiments will become apparent with reference to the drawings and detailed description that follow.

DETAILED DESCRIPTION

In the following detailed description of the illustrative, non-limiting embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is not to be taken in a limiting sense, and the scope of the illustrative embodiments are defined only by the appended claims.

Figure 1:
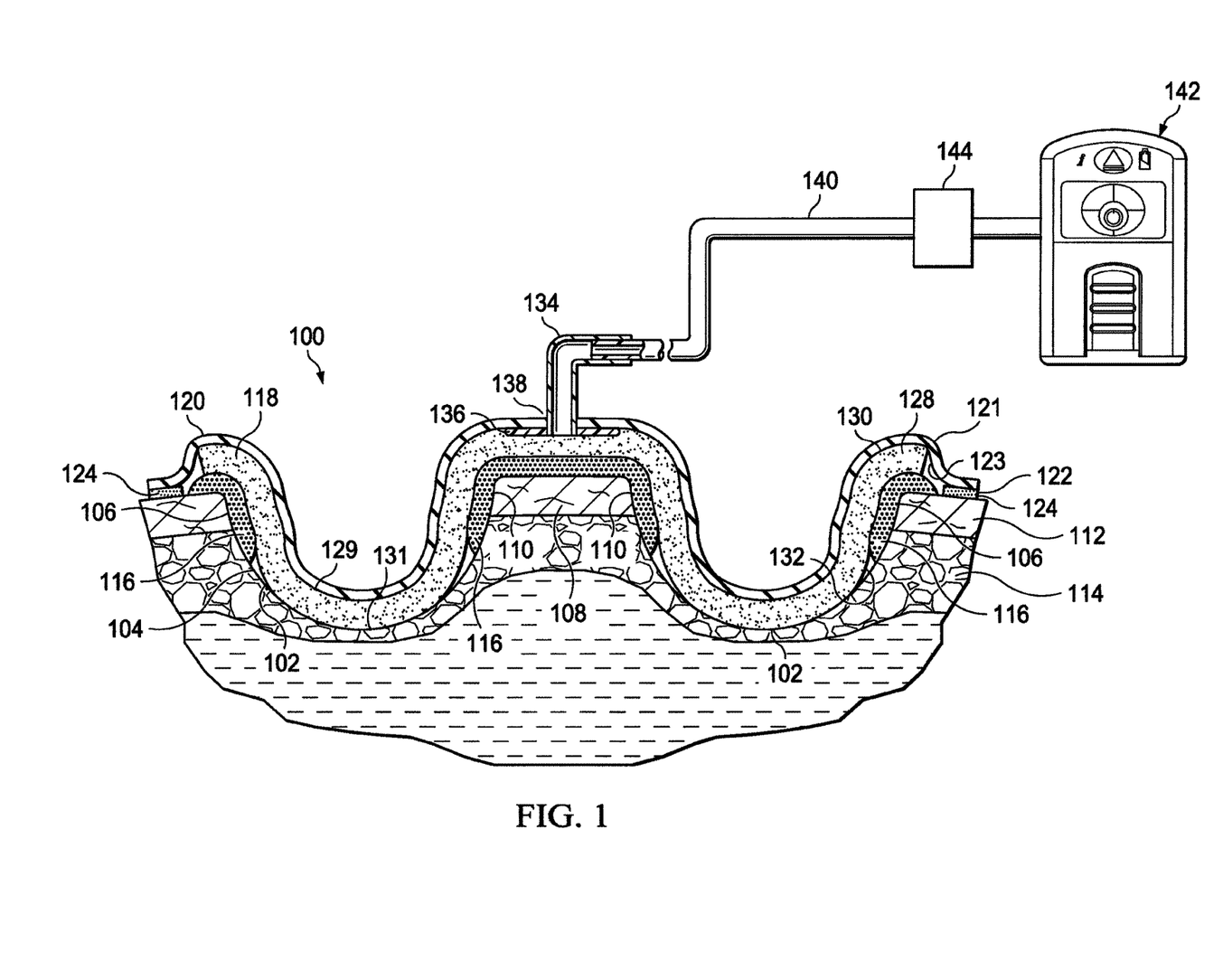
FIG. 1 is a schematic diagram with a portion in cross section of an illustrative, non-limiting embodiment of a system and dressing for re-epithelialization and granulation of a wound.

Referring now primarily to FIG. 1, an illustrative, non-limiting embodiment of a wound treatment system 100 that facilitates granulation and re-epithelialization is presented. The system 100 is shown deployed for treatment of a tissue site 102 and, in particular, a wound 104. The wound 104 is shown extending through epidermis 112 and into subcutaneous tissue 114. A peri-wound area may include the wound 104 and intact tissue near the wound 104 or may include the wound 104 alone. The tissue site 102 may be the bodily tissue of any human, animal, or other organism, including bone tissue, adipose tissue, muscle tissue, dermal tissue, vascular tissue, connective tissue, cartilage, tendons, ligaments, or any other tissue. The wound treatment system 100 facilitates re-epithelialization of a portion of the tissue site 102 and facilitates granulation of another portion of the tissue site 102 with both potentially occurring at the same time. The wound 104 may have wound edges 106 and may include one or more islands of intact epidermis, such as island 108 of intact epidermis, which has wound edges 110. The wound 104 may be regarded as including wound edges 106, 110.

The epithelialization, or re-epithelialization, phase of acute wound healing involves resurfacing of the wound 104 and changes in the wound edges 106, 110. The process protects a patient's body from invasion by outside organisms and may occur concurrently with other phases if not restricted. The resurfacing aspect involves keratinocytes.

Among other things, keratinocytes form layers of the dermis and epidermis. Keratinocytes are derived from epidermal stem cells located in the bulge area of hair follicles and migrate from that location into the basal layers of epidermis. The keratinocytes proliferate and differentiate to produce epidermis and thereby replenish the epidermis. Keratinocytes may respond to signals released from growth factors, which may be in wound exudate, by advancing in a sheet to resurface a space. Because of this migration, a moist wound environment may speed the migration of keratinocytes toward one another from the wound edges 106, 110. The wound treatment system 100 promotes the re-epithelialization phase or process and the granulation phase or process.

The wound treatment system 100 includes a moist barrier 116, a reduced-pressure treatment dressing 118, and a sealing member 120. When the wound treatment system 100 is deployed, the reduced-pressure treatment dressing 118 will be disposed adjacent to portions of the tissue site 102 where primarily granulation is desired and adjacent the moist barrier 116 in other locations. The moist barrier 116 will be adjacent to portions of the tissue site 102 where primarily re-epithelialization is to be promoted and where granulation is to be inhibited or not facilitated. Among other things, the moist barrier 116 reduces or prevents reduced pressure from being experienced at the location covered by the moist barrier 116 or reduces or prevents contact by a micro-strain-inducing surface of a manifold 128 of the reduced-pressure treatment dressing 118.

After the moist barrier 116 is deployed at the desired location, e.g., the wound edges 106, 110, and the reduced-pressure treatment dressing 118 is placed over the tissue site 102 and the moist barrier 116, the sealing member 120 is deployed. The sealing member 120 is deployed over the reduced-pressure treatment dressing 118 and a portion of a patient's intact epidermis 112.

The sealing member 120 has a first side 121 and a second, tissue-facing side 123. The sealing member 120 may be formed from any material that provides a fluid seal. "Fluid seal," or "seal," means a seal adequate to maintain reduced pressure at a desired site given the particular reduced-pressure source or subsystem involved. The sealing member may, for example, be an impermeable or semi-permeable, elastomeric material. "Elastomeric" means having the properties of an elastomer. Elastomer generally refers to a polymeric material that has rubber-like properties. More specifically, most elastomers typically have ultimate elongations greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. Additional examples of sealing member materials include a silicone drape, 3M Tegaderm® drape, polyurethane (PU) drape such as one available from Avery Dennison Corporation of Pasadena, Calif.

An attachment device 122 may be used to form a fluid seal between the epidermis 112 and the sealing member 120. The attachment device 122 may be used to hold the sealing member 120 against the patient's epidermis 112 or another layer, such as a gasket or additional sealing member. The attachment device 122 may take numerous forms. For example, the attachment device 122 may be a medically acceptable, pressure-sensitive adhesive 124 that extends about a periphery of the sealing member 120.

The reduced-pressure treatment dressing 118, which has a first side 130 and a second, tissue-facing side 132, may be any dressing that distributes reduced pressure and that may help promote micro-strain at the tissue site 102. For example, the reduced-pressure treatment dressing 118 may be or include the manifold 128. The term "manifold" as used herein generally refers to a substance or structure that is provided to assist in applying reduced pressure to, delivering fluids to, or removing fluids from the tissue site 102. The manifold 128 typically includes a plurality of flow channels or pathways that distribute fluids provided to and removed from the tissue site 102 around the manifold 128. In one illustrative, non-limiting embodiment, the flow channels or pathways are interconnected to improve distribution of fluids provided or removed from the tissue site 102. The manifold 128 may be a biocompatible material that is capable of being placed in contact with the tissue site 102 and distributing reduced pressure to the tissue site 102.

Examples of the manifold 128 may include, for example, without limitation, devices that have structural elements arranged to form flow channels, such as, for example, cellular foam, open-cell foam, porous tissue collections, liquids, gels, and foams that include, or cure to include, flow channels. The manifold 128 may be porous and may be made from foam, gauze, felted mat, or any other material suited to a particular biological application. In one embodiment, the manifold 128 is a porous foam and includes a plurality of interconnected cells or pores that act as flow channels. The porous foam may be a polyurethane, open-cell, reticulated foam, such as GranuFoam® material manufactured by Kinetic Concepts, Incorporated of San Antonio, Tex. Other embodiments may include "closed cells." The manifold 128 has a first side 129 and a second, tissue-facing side 131. The second, tissue-facing side 131 may provide a micro-strain-inducing surface, such as open cells or protrusions or other devices that impinge on the tissue site 102 when under reduced pressure or a force.

In one embodiment, the manifold 128 may be constructed from bioresorbable materials that do not have to be removed from a patient's body following use of the reduced-pressure treatment dressing 118. Suitable bioresorbable materials may include, without limitation, a polymeric blend of polylactic acid (PLA) and polyglycolic acid (PGA). The polymeric blend may also include without limitation polycarbonates, polyfumarates, and capralactones. The manifold 128 may further serve as a scaffold for new cell-growth, or a scaffold material may be used in conjunction with the manifold 128 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some situations, the manifold 128 may also be used to distribute fluids, such as medications, antibacterials, growth factors, and various solutions to the tissue site 102. Other layers may be included in or on the manifold 128, such as absorptive materials, wicking materials, hydrophobic materials, and hydrophilic materials.

A reduced-pressure connector 134 may be associated with the reduced-pressure treatment dressing 118 to provide reduced pressure thereto. The reduced-pressure connector 134 may have a flange portion 136 that may be disposed between the sealing member 120 and the first side 130 of the reduced-pressure treatment dressing 118. A portion of the reduced-pressure connector 134 extends through a connector aperture 138 in the sealing member 120. A reduced-pressure delivery conduit 140 may be used to fluidly couple the reduced-pressure connector 134 to a reduced-pressure source 142. One or more devices 144 may be associated or fluidly coupled to the reduced-pressure delivery conduit 140. The device or devices 144 that may be fluidly coupled to the reduced-pressure delivery conduit 140 include, for example, without limitation, a fluid reservoir or collection member to hold exudates and other fluids removed, a pressure-feedback device, a volume detection system, a blood detection system, an infection detection system, a flow monitoring system, a temperature monitoring system, or other device.

The reduced-pressure source 142 provides reduced pressure as a part of the system 100. The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure of tissue at the tissue site. Although the terms "vacuum" and "negative pressure" may be used to describe the pressure applied to the tissue site, the actual pressure applied to the tissue site may be significantly more than the pressure normally associated with a complete vacuum. Unless otherwise indicated, values of pressure stated herein are gauge pressures.

The reduced pressure delivered by the reduced-pressure source 142 may be constant or varied (patterned or random) and may be delivered continuously or intermittently. In order to maximize patient mobility and ease, the reduced-pressure source 142 may be a battery-powered, reduced-pressure generator. This facilitates application in the operating room and provides mobility and convenience for the patient during the rehabilitation phase. Other sources of reduced pressure might be utilized, such as V.A.C.® therapy unit, which is available from KCI of San Antonio, Tex., wall suction, a mechanical unit, or a micro-pump imbedded in the reduced-pressure treatment dressing 118. The pressure may in the range of −5 mm Hg to −500 mm Hg and more typically between −100 mm Hg and −200 mm Hg.

The reduced pressure developed by the reduced-pressure source 142 is delivered through the reduced-pressure delivery conduit 140, or medical conduit or tubing, to the reduced-pressure connector 134. A hydrophobic membrane filter may be interspersed between the reduced-pressure delivery conduit 140 and the reduced-pressure source 142. In another illustrative embodiment, reduced pressure is delivered by a micro-pump to a sealed spaced under the sealing member 120.

The moist barrier 116 may be formed from numerous materials. In one illustrative, non-limiting embodiment, the moist barrier 116 is a moist, water-sensitive barrier, such as a hydrogel, hydrocolloid, or other part solid solution. The moist barrier 116 may also be a substance in a foam formulation such as a hydrogel or hydrocolloid foam form or may be an emulsified oil. The material from which the moist barrier 116 is formed may be water-sensitive, or a fluid balancing material, meaning that the material will provide moisture to dry wounds and will absorb moisture from excessively moist, or wet, wounds. In one illustrative, non-limiting embodiment, the moist barrier 116 may be a water-sensitive, flowable material 146, such as a flowable hydrogel or flowable hydrocolloid. The moist barrier 116 may include additional substances, such as growth factors. The moist barrier 116 may promote bio-mimicry.

The water-sensitive, flowable material 146 may be a high viscosity fluid, like a flowable hydrogel or hydrocolloid that is low enough in viscosity to flow, but high enough in viscosity to occlude the reduced-pressure treatment dressing 118. The water-sensitive, flowable material 146 may move partially into the manifold 128. The degree to which the water-sensitive, flowable material 146 moves into the manifold 128 is, in the case of a foam manifold, governed primarily by pore size, the level of reduced pressure, and the viscosity of the water-sensitive, flowable material 146. For example, with a relatively viscous embodiment of the water-sensitive, flowable material 146 against a fine pore size foam, a majority of the water-sensitive, flowable material 146 will remain at the interface of the water-sensitive, flowable material 146 and the foam.

As an illustrative, non-limiting example, the water-sensitive, flowable material 146 may have a viscosity in the range of 2,000 to 250,000 centipoise (cP) at 25° C. As another illustrative, non-limiting example, the water-sensitive, flowable material 146 may have a viscosity in the range of 50,000 to 150,000 cP at 25° C. In another illustrative, embodiment, the water-sensitive, flowable material 146 may be a gel that is pseudoplastic (capable of shear thinning, i.e., shear dependent viscosity) so that the material has a low viscosity as dispensed with high shear, but once in place with a low shear situation, the material increases in viscosity.

Figure 2:
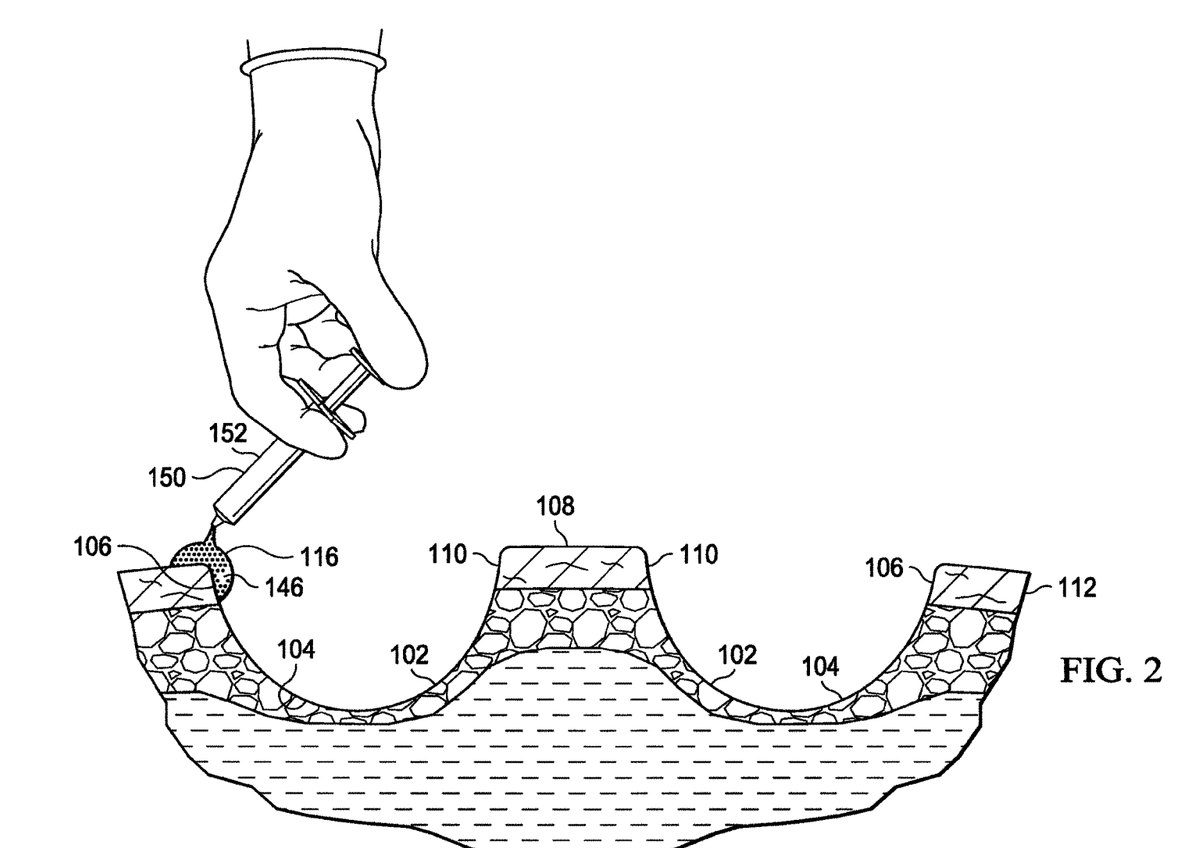
FIG. 2 is a schematic, cross-sectional view of a wound to which a moist, water-sensitive barrier is being applied to a portion of the tissue.

The moist barrier 116 is typically deployed in a position to cover the wound edges 106, 110 and may be deployed in a number of ways. Referring now primarily to FIG. 2, one illustrative, non-limiting description of a process for forming the moist barrier 116 is presented. In this illustrative example, the moist barrier 116 comprises the water-sensitive, flowable material 146. A delivery device 150, such as a squirtable container of material, a syringe 152, or other device, is used to deliver the water-sensitive, flowable material 146 directly to portions of the tissue site 102 where granulation is not desired, but re-epithelialization is desired. In this way, the moist barrier 116 is formed in situ. The water-sensitive, flowable material 146 may provide a moist environment for the portions of the tissue site 102 that are covered by the water-sensitive, flowable material 146, and the water-sensitive, flowable material 146 restricts or prevents reduced pressure from being delivered through the reduced-pressure treatment dressing 118 to the covered tissue or otherwise prevents micro-strain from being induced at the covered locations. In the illustrative example in which the reduced-pressure treatment dressing 118 is formed from an open cell foam, the water-sensitive, flowable material 146 may occlude cells that contact the water-sensitive, flowable material 146.

Figure 3:
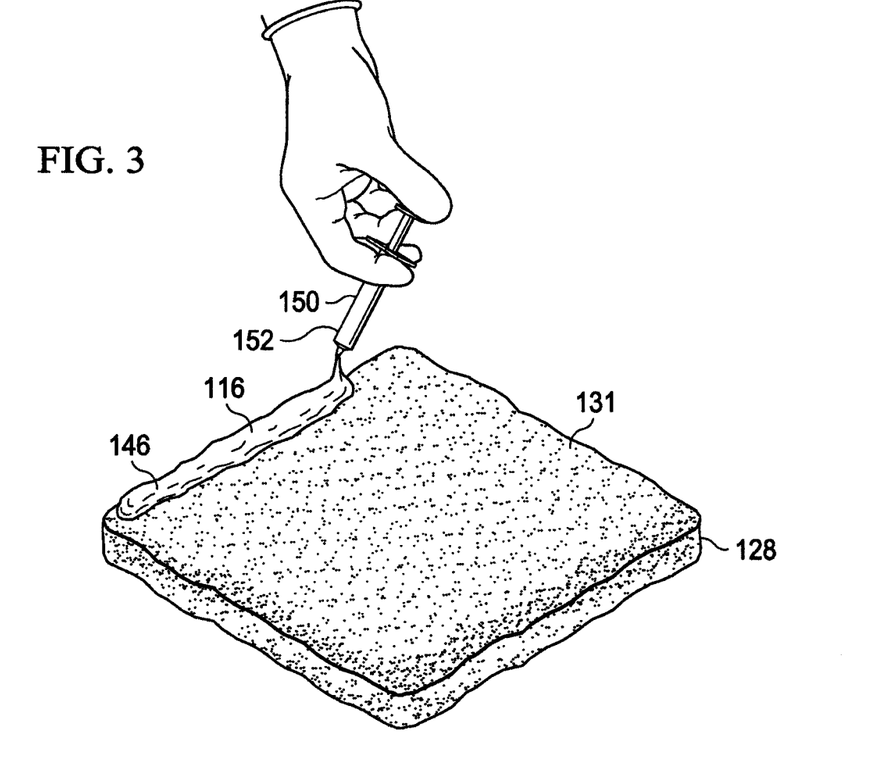
FIG. 3 is a schematic, perspective view of water-sensitive, flowable material being applied to a reduced-pressure treatment dressing.

Referring now primarily to FIG. 3, another illustrative, non-limiting example of how the moist barrier 116 may be formed is presented. In this illustrative, non-limiting embodiment, the delivery device 150, e.g., the syringe 152, is used to apply a water-sensitive, flowable material 146 onto the second, tissue-facing side 131 of the manifold 128. The water-sensitive, flowable material 146 is applied at locations on the second, tissue-facing side 131 of the manifold 128 that correspond or align, when deployed, with the portions of the tissue site 102 where granulation is not desired and re-epithelialization is desired. Thus, once the water-sensitive, flowable material 146 is applied to the second, tissue-facing side 131 of the manifold 128 and the manifold 128 is deployed adjacent to the tissue site 102, only the desired portions of the tissue site 102 will receive reduced pressure in operation.

Figure 4:
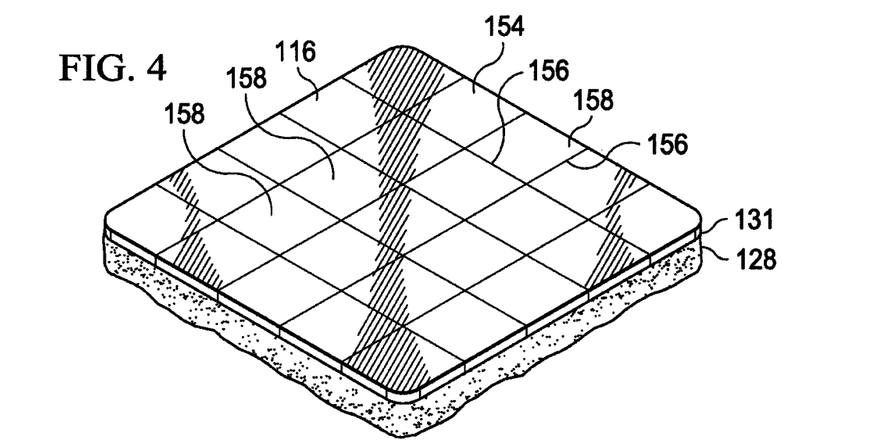
FIG. 4 is a schematic, perspective view of an illustrative, non-limiting embodiment of a wound dressing.

Referring now primarily to FIG. 4, still another illustrative, non-limiting example of how the moist barrier 116 may be formed is presented. In this illustrative example, a layer 154 of water-sensitive material is applied to the second, tissue-facing side 131 of the manifold 128 and substantially covers the second, tissue-facing side 131 of the manifold 128. The layer 154 includes perforations or cuts 156 that readily allow one to remove one or more segments, or portions 158, of the layer 154 to expose a portion of the second, tissue-facing side 131 of the manifold 128. As such, the segments 158 may be removed that correspond, when deployed, to portions of the tissue site 102 where granulation is desired. When the reduced-pressure treatment dressing 118 is deployed with the second, tissue-facing side 131 adjacent the tissue site 102, the remaining portions of the layer 154 that form the moist barrier 116 will be adjacent to the areas where no granulation is desired but re-epthiliazation is desired. At the same time, the second, tissue-facing side 131 of the manifold 128 will be against the portions of the tissue site 102 where granulation is desired.

According to one illustrative, non-limiting embodiment, the moist barrier 116 may be formed from a hydrogel, hydrocolloid, or other material. In this embodiment, the hydrogel or hydrocolloid may be cast onto a woven liner and cross-linked. In this illustrative embodiment, the hydrogrel or hydrocolloid is not mobile.

According to one illustrative, non-limiting method of deploying the wound treatment system 100, the moist barrier 116 is placed adjacent to the portion of the tissue site 102 where granulation is not desired and where re-epithelialization is desired. The second, tissue-facing side 131 of the manifold 128 is placed directly adjacent to the portion of the tissue site 102 where granulation is desired. The sealing member 120 is placed over the tissue site 102 and a portion of the patient's intact epidermis 112 to form a fluid seal. Reduced pressure is supplied to the manifold 128.

A kit for deploying a dressing for promoting granulation and re-epithelialization of a wound of a patient may be formed that provides an easy and convenient manner to treat a wound. The kit may include a reduced-pressure treatment dressing (e.g., reduced-pressure treatment dressing 118) and a water-sensitive, flowable material (e.g., water-sensitive, flowable material 146) for disposing adjacent to the reduced-pressure treatment dressing (e.g., reduced-pressure dressing 118) at locations on the wound where granulation is not desired and where re-epithelialization is desired. The kit also may include a sealing member (e.g., sealing member 120) for placing over the reduced-pressure treatment dressing and a portion of epidermis of the patient and may include a reduced-pressure delivery conduit (e.g., reduced-pressure delivery conduit 140) for providing reduced pressure to the reduced-pressure treatment dressings. The kit may include a delivery device (e.g., delivery device 150) for applying the water-sensitive, flowable material and may include a reduced-pressure connector (e.g., reduced-pressure connector 134).

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in a connection to any one embodiment may also be applicable to any other embodiment.

We claim:

1. A method for promoting granulation and re-epithelialization of a wound, the method comprising:
    applying a hydrogel to a first portion of the wound;
    placing a reduced-pressure treatment dressing configured to distribute reduced pressure and having a micro-strain-inducing surface for promoting granulation over the wound and the hydrogel such that the hydrogel is disposed between a portion of the micro-strain-inducing surface and the first portion of the wound and is not disposed between the micro-strain-inducing surface and a second portion of the wound;
    applying a sealing member over the reduced-pressure treatment dressing, hydrogel, and a portion of epidermis; and
    applying reduced pressure to the reduced-pressure treatment dressing,
    wherein the hydrogel restricts delivery of the reduced pressure to the first portion of the wound to promote re-epithelialization and inhibit granulation at the first portion of the wound, and
    wherein the hydrogel does not restrict delivery of the reduced pressure to the second portion of the wound to promote granulation at the second portion of the wound.

2. The method of claim 1, wherein the hydrogel comprises a flowable material.

3. The method of claim 2, wherein the hydrogel has a viscosity in the range of 50,000 to 150,000 cP at 25° C.

4. The method of claim 1, wherein the reduced-pressure treatment dressing comprises a manifold.

5. The method of claim 1, wherein the micro-strain-inducing surface is an open-cell foam.

6. The method of claim 1, wherein applying the hydrogel comprises using a delivery device to align with tissue locations where it is desirable to encourage re-epithelialization and inhibit granulation.

7. The method of claim 6, wherein the delivery device comprises a syringe to deliver the hydrogel onto the micro-strain-inducing surface.

8. The method of claim 1, wherein the micro-strain-inducing surface is a gauze.

9. A method for promoting granulation and re-epithelialization of a tissue site, comprising:
    disposing a hydrogel barrier adjacent to a first portion of a tissue-facing side of a reduced-pressure treatment dressing configured to distribute reduced pressure;
    applying the reduced-pressure treatment dressing to the tissue site such that the hydrogel barrier is disposed between the first portion of the tissue-facing side of the reduced-pressure treatment dressing and a first portion of the tissue site and is not disposed between tissue-facing side of the reduced-pressure treatment dressing and a second portion of the tissue site;
    placing a sealing member over the reduced-pressure treatment dressing; and
    providing reduced pressure to the reduced-pressure treatment dressing;
    wherein the hydrogel barrier restricts delivery of the reduced pressure to the first portion of the tissue site to promote re-epithelialization and inhibit granulation at the first portion of the tissue site, and
    wherein the hydrogel does not restrict delivery of the reduced pressure to the second portion of the tissue site to promote granulation at the second portion of the tissue site.

10. The method of claim 9, further comprising:
disposing a reduced-pressure connector in fluid communication with the reduced-pressure treatment dressing; and
connecting a reduced-pressure delivery conduit to the reduced-pressure connector and a reduced-pressure source.

11. The method of claim 9, wherein the tissue-facing side of the reduced-pressure treatment dressing comprises a manifold adapted to deliver reduced pressure to the tissue site.

12. A method for promoting granulation and re-epithelialization of a wound, comprising:
perforating a layer of water-sensitive material to divide the layer into segments;
applying the layer of water-sensitive material to a tissue-facing side of a manifold;
removing one or more segments of the layer to expose an exposed portion of the tissue-facing side of the manifold while leaving one or more segments of the layer applied to an unexposed portion of the tissue-facing side of the manifold;
applying the manifold to the wound such that the remaining one or more segments of the layer are disposed between a first portion of the wound where re-epithelialization is desired and the unexposed portion of the tissue-facing side of the manifold and such that no segments of the layer of water-sensitive material are disposed between a second portion of the wound where granulation is desired and the exposed portions of the tissue-facing side of the manifold; and
providing reduced pressure to the manifold,
wherein the layer of water-sensitive material restricts delivery of the reduced pressure to the first portion of the wound to promote re-epithelialization and inhibit granulation at the first portion of the wound, and
wherein the layer of water-sensitive material does not restrict delivery of the reduced pressure to the second portion of the wound to promote granulation at the second portion of the wound.

13. The method of claim 12, further comprising forming a fluid seal over the manifold.

14. The method of claim 1, wherein the hydrogel is applied to an interface comprising the first portion of the wound and a portion of adjacent epidermis is at least partially located interior to outer portions of the sealing member.

15. The method of claim 14, wherein the portion of the adjacent epidermis comprises an island of intact epidermis.

16. The method of claim 12, wherein the layer is applied to a portion of adjacent epidermis comprising an island of intact epidermis.

* * * * *